United States Patent

Dang

[19]

[11] Patent Number: 5,935,162
[45] Date of Patent: Aug. 10, 1999

[54] WIRE-TUBULAR HYBRID STENT

[75] Inventor: Kenny L. Dang, San Diego, Calif.

[73] Assignee: Medtronic, Inc., Minneapolis, Minn.

[21] Appl. No.: 09/039,671

[22] Filed: Mar. 16, 1998

[51] Int. Cl.[6] .................................................. A61F 2/06
[52] U.S. Cl. ................................................ 623/1; 623/12
[58] Field of Search .......................... 623/1, 12; 606/194

[56] References Cited

U.S. PATENT DOCUMENTS

| | | | |
|---|---|---|---|
| 5,135,536 | 8/1992 | Hillstead | 606/195 |
| 5,292,331 | 3/1994 | Boneau | 606/198 |
| 5,344,426 | 9/1994 | Lau et al. | 606/198 |
| 5,370,683 | 12/1994 | Fontaine | 623/1 |
| 5,514,154 | 5/1996 | Lau et al. | 606/195 |
| 5,569,295 | 10/1996 | Lam | 606/198 |
| 5,591,197 | 1/1997 | Orth et al. | 606/198 |
| 5,603,721 | 2/1997 | Lau et al. | 606/195 |
| 5,636,641 | 6/1997 | Fariabi | 623/1 |
| 5,674,278 | 10/1997 | Boneau | 623/1 |
| 5,695,516 | 12/1997 | Fischell et al. | 606/194 |
| 5,735,893 | 4/1998 | Lau et al. | 623/12 |
| 5,755,776 | 5/1998 | Al-Saadon | 623/12 |
| 5,776,161 | 7/1998 | Globerman | 606/194 |
| 5,776,183 | 7/1998 | Kanesaka et al. | 623/1 |
| 5,800,521 | 9/1998 | Orth | 623/1 |
| 5,800,526 | 9/1998 | Anderson et al. | 606/194 |
| 5,843,120 | 12/1998 | Israel | 623/1 |
| 5,843,175 | 12/1998 | Frantzen | 623/1 |
| 5,851,228 | 12/1998 | Pinheiro | 623/1 |
| 5,855,600 | 1/1999 | Alt | 623/1 |

FOREIGN PATENT DOCUMENTS

WO 97/21399  6/1997  WIPO.

OTHER PUBLICATIONS

GFX Brochure—Bridging the Gap In Stent Technology, AVE (Arterial Vascular Engineering) 1996, GFX.USO896.

*Primary Examiner*—Paul J. Hirsch
*Attorney, Agent, or Firm*—Kevin W. Raasch; Dianne Plunkett Latham; Harold R. Patton

[57] ABSTRACT

Radially-expandable stents are provided with improved longitudinal flexibility and stability, improved torsional flexibility and stability, improved trackability and conformability, and improved hoop strength. The stents combine the advantages typically associated with wire stents with those typically associated longitudinal stability. The stents include a plurality of cylindrical sections successively arranged along a longitudinal axis of the stent, a plurality of W-shaped elements in each of the cylindrical sections, each of the W-shaped elements having a center section and two outside legs, the plurality of W-shaped elements in each of the cylindrical sections opening in alternating directions along the longitudinal axis of the stent, wherein the W-shaped elements in adjacent cylindrical sections alternate between pairs of W-shaped elements that open towards each other along the longitudinal axis and pairs of W-shaped elements that open away from each other along the longitudinal axis when moving about the circumference of the adjacent cylindrical sections; and a plurality of tie members connecting adjacent cylindrical sections along the longitudinal axis of the stent, the tie members connecting center sections of the pairs of W-shaped elements that open towards each other along the longitudinal axis in each pair of adjacent cylindrical sections. Methods of implanting the stents in body lumens are also disclosed.

18 Claims, 7 Drawing Sheets

5,935,162

WIRE-TUBULAR HYBRID STENT

FIELD OF THE INVENTION

The present invention relates to intravascular stent implants for maintaining vascular patency in humans and animals and more particularly to a stent having a plurality of radially expandable sections interconnected along the longitudinal length of the stent.

BACKGROUND OF THE INVENTION

Percutaneous transluminal coronary angioplasty (PTCA) is used to increase the lumen diameter of a coronary artery partially or totally obstructed by a build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen.

Dilatation of the occlusion, however, can form flaps, fissures and dissections which threaten reclosure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. It has also been shown that the use of intravascular stents can measurably decrease the incidence of restenosis after angioplasty thereby reducing the likelihood that a secondary angioplasty procedure or a surgical bypass operation will be necessary.

An implanted prosthesis such as a stent can preclude additional procedures and maintain vascular patency by mechanically supporting dilated vessels to prevent vessel reclosure. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver. The body lumens range in diameter from small coronary vessels of 3 mm or less to 28 mm in the aortic vessel. The invention applies to acute and chronic closure or reclosure of body lumens.

A typical stent is a cylindrically shaped wire formed device intended to act as a permanent prosthesis. A typical stent ranges from 5 mm to 50 mm in length. A stent is deployed in a body lumen from a radially compressed configuration into a radially expanded configuration which allows it to contact and support a body lumen. The stent can be made to be radially self-expanding or expandable by the use of an expansion device. The self expanding stent is made from a resilient springy material while the device expandable stent is made from a material which is plastically deformable. A plastically deformable stent can be implanted during a single angioplasty procedure by using a balloon catheter bearing a stent which has been crimped onto the balloon. Stents radially expand as the balloon is inflated, forcing the stent into contact with the interior of the body lumen thereby forming a supporting relationship with the vessel walls.

Conventional angioplasty balloons fall into high, medium and low pressure ranges. Low pressure balloons are those which fall into rated burst pressures below 6 atm. Medium pressure balloons are those which fall into rated burst pressures between 6 and 12 atm. High pressure balloons are those which fall into rated burst pressures above 12 atm. Burst pressure is determined by material selection, wall thickness and tensile strength.

The biocompatible metal stent props open blocked coronary arteries, keeping them from reclosing after balloon angioplasty. A balloon of appropriate size and pressure is first used to open the lesion. The process is repeated with a stent crimped on a second balloon. The second balloon may be a high pressure type of balloon, e.g., more than 12 atmospheres, to insure that the stent is fully deployed upon inflation. The stent is deployed when the balloon is inflated. The stent remains as a permanent scaffold after the balloon is withdrawn. A high pressure balloon is preferable for stent deployment because the stent must be forced against the artery's interior wall so that it will fully expand thereby precluding the ends of the stent from hanging down into the channel encouraging the formation of thrombus.

Although many stents are made of wire wound and bent into desired configurations, stents may also be formed using thin-walled tubes that are laser cut or otherwise formed to allow the tubes to be compressed into a smaller diameter for delivery to a desired location within a body lumen. Such stents, commonly referred to as tubular stents, provide advantages in terms of increased torsional stability and hoop strength as compared to stents formed from wires. One disadvantage, however, is that such stents typically exhibit limited longitudinal flexibility which can limit delivery through tortuous pathways and their deployment in curved body lumens.

As a result, a need exists for a stent that provides the longitudinal flexibility associated with wire-wound stents in combination with the hoop strength and torsional stability of a tubular stent.

SUMMARY OF THE INVENTION

It is an object of the invention to provide a stent having good longitudinal flexibility to maneuver through tortuous vessels and other body lumens similar to wire stents.

It is another object of the present invention to provide a stent having radial or hoop strength similar to tubular stents.

It is a further object of the present invention to provide a stent having good torsional stability similar to tubular stents.

It is a further object of the present invention to provide a stent having good longitudinal stability.

In one aspect, the present invention provides a radially expandable stent for implantation within a body vessel including a plurality of cylindrical sections successively arranged along a longitudinal axis of the stent; a plurality of W-shaped elements in each of the cylindrical sections, each of the W-shaped elements including a center section and two outside legs, the plurality of W-shaped elements in each of the cylindrical sections opening in alternating directions along the longitudinal axis of the stent, wherein the W-shaped elements in adjacent cylindrical sections alternate between pairs of W-shaped elements that open towards each other along the longitudinal axis and pairs of W-shaped elements that open away from each other along the longitudinal axis when moving about the circumference of the adjacent cylindrical sections; and a plurality of tie members connecting adjacent cylindrical sections along the longitudinal axis of the stent, the tie members connecting center sections of the pairs of W-shaped elements that open towards each other along the longitudinal axis in each pair of adjacent cylindrical sections.

In another aspect, the present invention provides a radially expandable stent for implantation within a body vessel including a plurality of cylindrical sections successively arranged along a longitudinal axis of the stent; a plurality of W-shaped elements in each of the cylindrical sections, each of the W-shaped elements including a center section and two outside legs, wherein the center section of each of the W-shaped elements is shorter in the longitudinal direction than the outside legs of the W-shaped element, the plurality of W-shaped elements in each of the cylindrical sections opening in alternating directions along the longitudinal axis of the stent, wherein the W-shaped elements in adjacent cylindrical sections alternate between pairs of W-shaped elements that open towards each other along the longitudinal axis and pairs of W-shaped elements that open away from each other along the longitudinal axis when moving about the circumference of the adjacent cylindrical sections; and a plurality of tie members connecting adjacent cylindrical sections along the longitudinal axis of the stent, the tie members connecting center sections of the pairs of W-shaped elements that open towards each other along the longitudinal axis in each pair of adjacent cylindrical sections; wherein the stent comprises first, second, and third cylindrical sections arranged along the longitudinal axis in that order, and further wherein the tie members connecting the center sections of the pairs of W-shaped elements that open towards each other in the first and second cylindrical sections are offset about the circumference of the stent from the tie members connecting the centers of the pairs of W-shaped elements that open towards each other in the second and third cylindrical sections.

In another aspect, the present invention provides a method of implanting a radially expandable stent within a body lumen by providing radially expandable stent in a compressed state, the stent including a plurality of cylindrical sections successively arranged along a longitudinal axis of the stent; a plurality of W-shaped elements in each of the cylindrical sections, each of the W-shaped elements including a center section and two outside legs, the plurality of W-shaped elements in each of the cylindrical sections opening in alternating directions along the longitudinal axis of the stent, wherein the W-shaped elements in adjacent cylindrical sections alternate between pairs of W-shaped elements that open towards each other along the longitudinal axis and pairs of W-shaped elements that open away from each other along the longitudinal axis when moving about the circumference of the adjacent cylindrical sections; and a plurality of tie members connecting adjacent cylindrical sections along the longitudinal axis of the stent, the tie members connecting center sections of the pairs of W-shaped elements that open towards each other along the longitudinal axis in each pair of adjacent cylindrical sections; followed by advancing the stent to a desired location within a body lumen; and radially expanding the stent within the body lumen.

These and other features and advantages of the present invention are discussed below with respect to illustrative embodiments of the invention.

DETAILED DESCRIPTION OF THE PREFERRED EMBODIMENTS

The present invention provides radially-expandable stents that provide improved longitudinal flexibility and stability, improved torsional flexibility and stability, improved trackability and conformability, and improved hoop strength. In many respects, the stents according to the present invention combine the advantages typically associated with wire stents with those typically associated longitudinal stability.

Although the following discussion, along with the figures, describes illustrative preferred embodiments and methods according to the present invention, those skilled in the art will understand that variations are possible. For example, although stents having two or more cylindrical sections are described herein, it will be understood that stents manufactured according to the present invention could have any number of desired cylindrical sections needed to obtain a stent with a desired longitudinal length. Furthermore, it will be understood that the figures are schematic only, and that the relative dimensions of the various illustrated features are not intended to limit the scope of the present invention.

Figure 1:
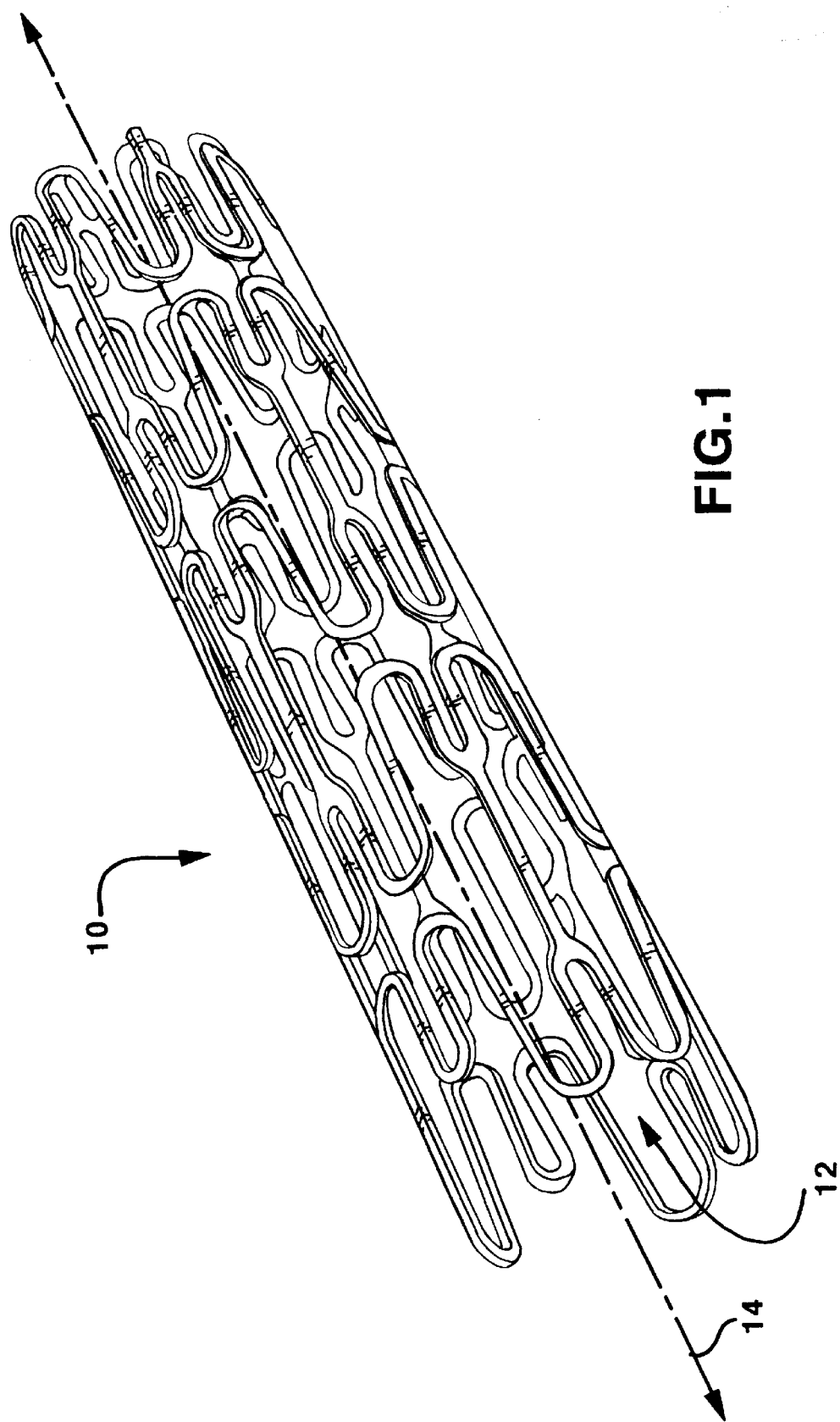
FIG. 1 is a perspective view of one stent according to the present invention.

FIG. 1 depicts one illustrative radially-expandable stent according to the present invention. The depicted stent 10 includes a generally tubular body defining a passageway 12 extending along a longitudinal axis 14. The stent 10 is preferably formed from a plurality of cylindrical sections 20a, 20b, 20c, 20d, and 20e (collectively referred to as cylindrical sections 20 below) arranged successively along the longitudinal axis 14.

The stent 10 is depicted in FIG. 1 in its expanded state in which the cylindrical sections 20 have been expanded radially outward from the longitudinal axis 14. Although not depicted, it will be understood that the stent 10 can be radially compressed into a smaller diameter to ease delivery of the stent 10 to a desired location within a body lumen where the stent 10 can then be radially expanded to provide the desired support to the lumen.

Figure 2:
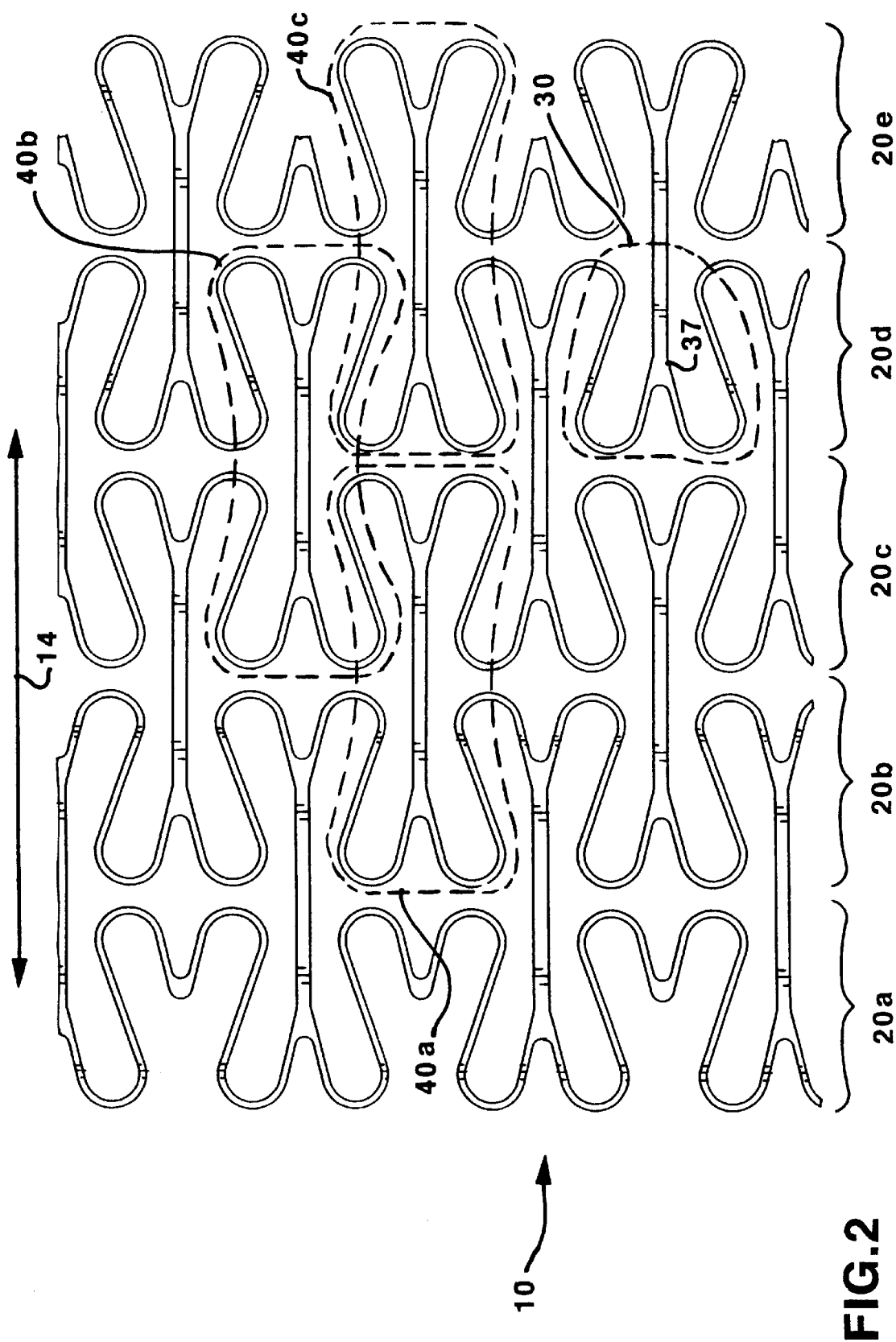
FIG. 2 is a plan view of the stent of FIG. 1 after unrolling the stent from its tubular shape.
Figure 3:
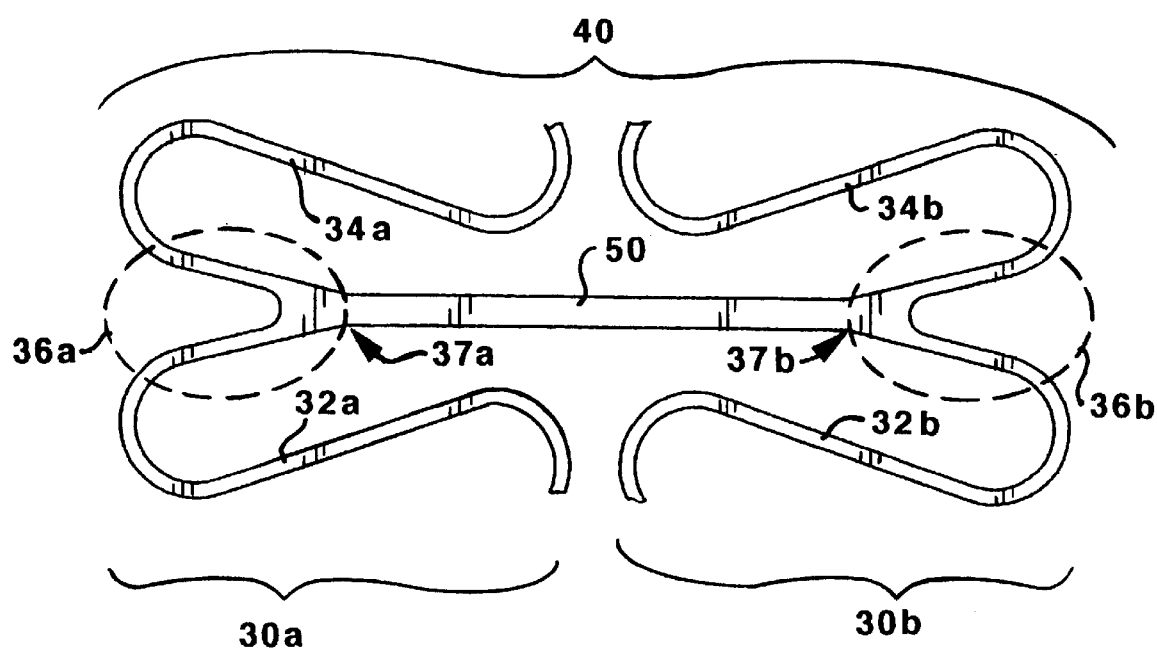
FIG. 3 is an enlarged view of a portion of the stent of FIGS. 1 and 2.

FIG. 2 is a plan view of a portion of the stent 10 depicted in FIG. 1 in which the body has been unrolled from the tubular shape of FIG. 1 and FIG. 3 is an enlarged view of a portion of FIG. 2. Each of the cylindrical sections 20 has a length along the longitudinal axis 14 and includes a plurality of W-shaped elements 30 (only one of which is denoted by a reference number). The W-shaped elements 30 open in alternating directions along the longitudinal axis 14 of the stent 10 about the perimeter or circumference of the cylindrical sections 20 (i.e., in the hoop direction).

Two W-shaped elements 30a and 30b (collectively referred to as W-shaped elements 30) in adjacent cylindrical sections 20b and 20c are depicted in FIG. 3. Each of the W-shaped elements 30 includes a center section 36a/36b and two outside legs 32a/32b and 34a/34b. In the design depicted in FIG. 2, the center sections 36a/36b of the W-shaped elements 30 terminate at peaks or apexes 37a/37b that are located at about the midpoint of the cylindrical sections 20, i.e., the midpoint along the longitudinal length of the cylindrical sections 20. Referring back to FIG. 2, it can be seen that the outside legs 32a/32b and 34a/34b are shared or common to the adjacent W-shaped element 30 within each of the cylindrical sections 20. It is preferred, but not required, that the bends in each of the W-shaped elements 30 are curved or rounded to reduce stress-concentration points in the stent 10.

The cylindrical sections 20 are preferably arranged such that the W-shaped elements 30 in adjacent cylindrical sections 20 alternate between pairs of W-shaped elements 30 that open towards each other and pairs of W-shaped elements 30 that open away from each other when moving around the perimeter or circumference of the stent 10 (i.e., transverse to the axis 14 in FIG. 2).

FIG. 3 depicts one such pair of W-shaped elements 30a and 30b that open towards each other from adjacent cylindrical sections 20. As depicted, the W-shaped elements 30a/30b are connected to each other by a tie member 50 that is attached to the center sections 36a/36b of each of the W-shaped elements 30a/30b. It is preferred that the tie members 50 are attached to the W-shaped elements 30 at the peak or apex 37 of the center sections 36 of the opposing W-shaped elements 30.

Because the W-shaped elements 30 in each of the cylindrical sections 20 open in opposite directions as one moves about the circumference of the stent 10, each of the cylindrical sections is alternating between attachment to the cylindrical sections on either side. As best seen in FIG. 2, cylindrical section 20c alternates between attachment via a tie member 50 to cylindrical section 20b on one side and attachment via a tie member 50 to cylindrical section 20d on the opposite side as one moves about the circumference of the stent 10 (transverse to the longitudinal axis 14 or in the hoop direction).

The pairs of W-shaped elements 30 that open towards each other in adjacent cylindrical sections 20 can be described as forming cells 40a, 40b, and 40c (collectively referred to as cells 40) as seen in FIG. 2. Because the cylindrical sections 20 are connected to the adjacent cylindrical sections 20 in an alternating fashion on opposing sides as described above, the cells 40a and 40c are aligned along the longitudinal axis 14. Cell 40b, which bridges the longitudinal gap between the abutting cells 40a and 40c, is offset from the cells 40a and 40c about the circumference of the stent 10 (i.e., in the hoop direction).

The result of the interconnections between the W-shaped elements 30 and the cells 40 formed by the W-shaped elements 30 in the stent 10 as shown is that forces along the longitudinal axis 14 of the stent 10 are dispersed about the circumference of the stent 10. Similarly, forces acting torsionally about axis 14 are also dispersed throughout the body of the stent 10. In addition, forces acting radially inward are also dispersed throughout the stent 10, thereby reducing localized stress concentration and improving the overall hoop strength of the stent 10. The dispersion of forces gives the stent 10 its unique combination of flexibility and stability in both the longitudinal direction, in torsion and in hoop strength.

Although these concepts have been described with reference to three successive cylindrical sections, it will be understood that the concepts can be extended along the entire length of a stent incorporating as few as two cylindrical sections or as many cylindrical sections as desired.

Figure 4:
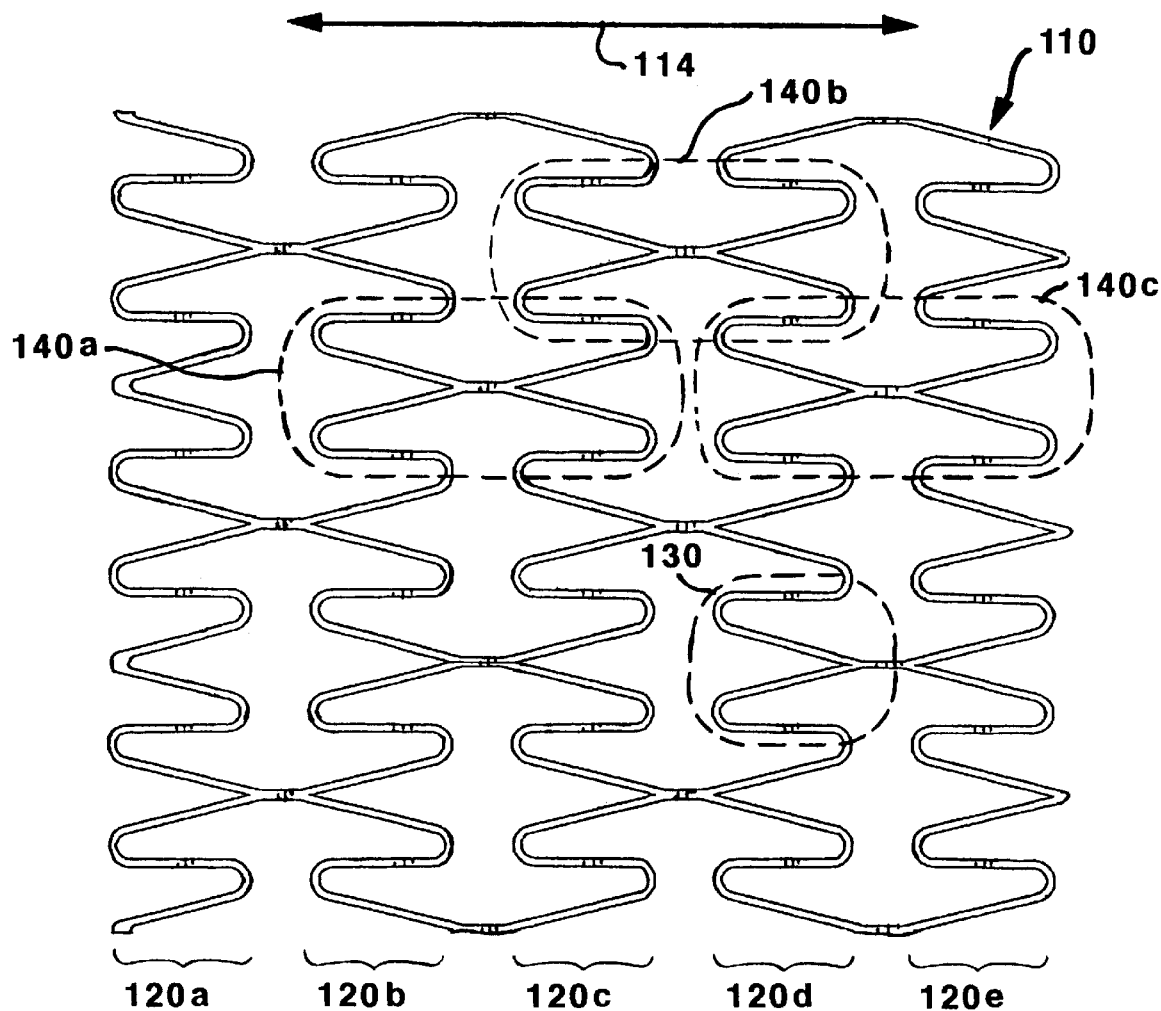
FIG. 4 is a plan view of an alternative stent according to the present invention after unrolling of the stent from its tubular shape.
Figure 5:
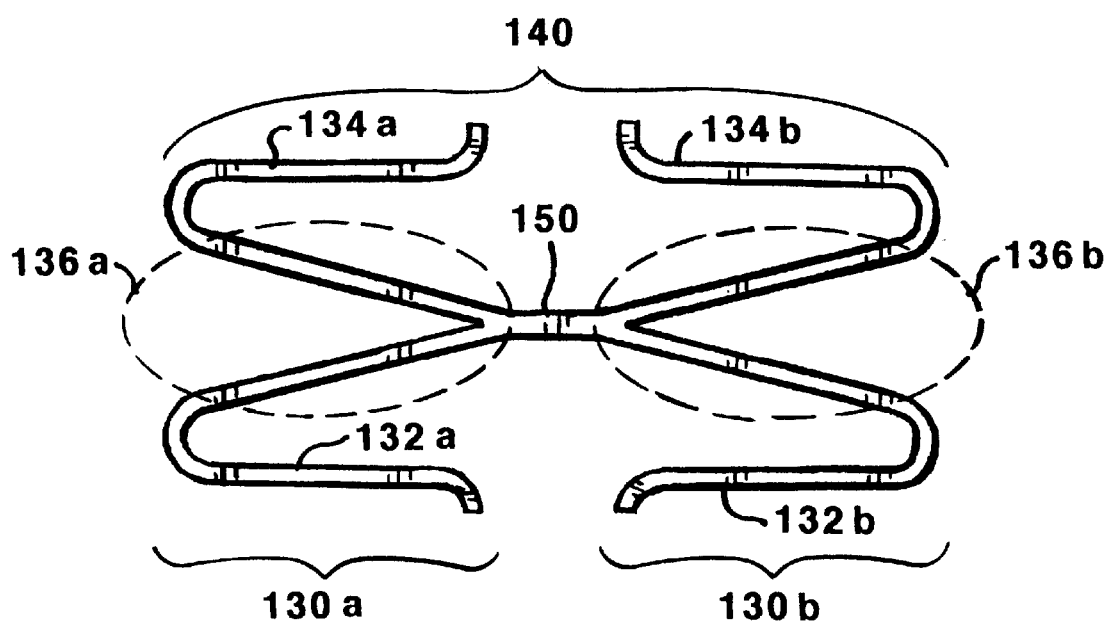
FIG. 5 is an enlarged view of a portion of the stent of FIG. 4.

FIGS. 4 and 5 depict an alternative embodiment of a stent 110 according to the present invention. FIG. 4 is a plan view of a portion of the body of the stent 110 in which the body has been unrolled from the tubular shape and FIG. 5 is an enlarged view of a portion of FIG. 4. As seen in FIG. 4, the stent 110 also includes cylindrical sections 120a, 120b, 120c, 120d, and 120e (collectively referred to as cylindrical sections 120) located successively along a longitudinal axis 114. Each of the cylindrical sections 120 has a length along the longitudinal axis 114 and includes a plurality of W-shaped elements 130 (only one of which is denoted by a reference number). The W-shaped elements 130 open in alternating directions along the longitudinal axis 114 of the stent 110 about the perimeter or circumference of the cylindrical sections 120 (i.e., in the hoop direction).

Two W-shaped elements 130a and 130b (collectively referred to as W-shaped elements 130) that open towards each other from adjacent cylindrical sections 120b and 120c are depicted in FIG. 5. Each of the W-shaped elements 130 includes a center section 136a/136b and two outside legs 132a/132b and 134a/134b. In the design depicted in FIG. 4, the center sections 136a/136b of the W-shaped elements 130 terminate at peaks or apexes 137a/137b that are generally aligned along one side of the cylindrical sections 120. Referring back to FIG. 4, it can be seen that the outside legs 132a/132b and 134a/134b are shared or common to the adjacent W-shaped element 130 within each of the cylindrical sections 120. It is preferred, but not required, that the bends between the outside legs 132a/132b and 134a/134b and the center sections 136a/136b are curved or rounded to reduce stress-concentration points in the stent 110.

The cylindrical sections 120 are preferably arranged such that the W-shaped elements 130 in adjacent cylindrical sections 120 alternate between pairs of W-shaped elements 130 that open towards each other and pairs of W-shaped elements 130 that open away from each other when moving around the perimeter or circumference of the stent 110 (i.e., transverse to the axis 114 in FIG. 4 or in the hoop direction).

FIG. 5 depicts one such pair of W-shaped elements 130a and 130b that open towards each other from adjacent cylindrical sections 120. As depicted, the W-shaped elements 130a/130b are connected to each other by a tie member 150 that is attached to the center sections 136a/136b of each of the W-shaped elements 130a/130b. Because the W-shaped elements 130 in each of the cylindrical sections 120 open in opposite directions as one moves about the circumference of the stent 110 (i.e., in the hoop direction), each of the cylindrical sections 120 alternates between attachment to the cylindrical sections 120 on either side. As best seen in FIG. 4, cylindrical section 120c alternates between attachment via a tie member 150 to cylindrical section 120b on one side and attachment via a tie member 150 to cylindrical section 120d on the opposite side as one moves about the circumference of the stent 110 (transverse to the longitudinal axis 114 or in the hoop direction).

The pairs of W-shaped elements 130 that open towards each other in adjacent cylindrical sections 120 can be described as forming cells 140a, 140b, and 140c (collectively referred to as cells 140) as seen in FIG. 4. Because the cylindrical sections 120 are connected to the adjacent cylindrical sections 120 in an alternating fashion on opposing sides as described above, the cells 140a and 140c are aligned along the longitudinal axis 114. Cell 140b, which bridges the longitudinal gap between the abutting cells 140a and 140c, is offset from the cells 140a and 140c about the circumference of the stent 110 (i.e., in the hoop direction).

The result of the interconnections between the cells 140 in the stent 110 as shown is that forces along the longitudinal axis 114 of the stent 110 are dispersed about the circumference of the stent 110. Similarly, forces acting torsionally on the stent 110 about axis 114 are also dispersed throughout the body of the stent 110. In addition, forces acting radially inward are also dispersed throughout the stent, thereby improving its hoop strength. The dispersion of forces gives the stent 110 its unique combination of flexibility and stability in both the longitudinal direction, in torsion and in hoop strength.

Although these concepts have been described with reference to three successive cylindrical sections, it will be understood that the concepts can be extended along the entire length of a stent incorporating as few as two cylindrical sections or as many cylindrical sections as desired.

It is significant to note that in stents manufactured according to the present invention, longitudinal bending flexibility is improved both when the stent is in the compressed state during delivery and upon deployment of the stent in its expanded state within a body lumen. Increased longitudinal bending flexibility when compressed permits threading of the stent through long tortuous vessels and lesions. Increased longitudinal bending flexibility when expanded allows for deployment in highly curved vessels or lumens.

Furthermore, the longitudinal flexibility of the stents 10/110 according to the present invention can be adjusted by varying the length of the tie members 50/150 connecting the cylindrical sections 20/120. Typically, a shorter tie member will improve longitudinal flexibility and a longer tie member will decrease longitudinal flexibility. Longitudinal flexibility must however, be balanced with torsional stability and the decrease in tie member length to obtain increased longitudinal flexibility may result in reduced torsional stability. Correspondingly, increasing the length of the tie members can increase torsional stability while decreasing longitudinal flexibility.

Figure 6:
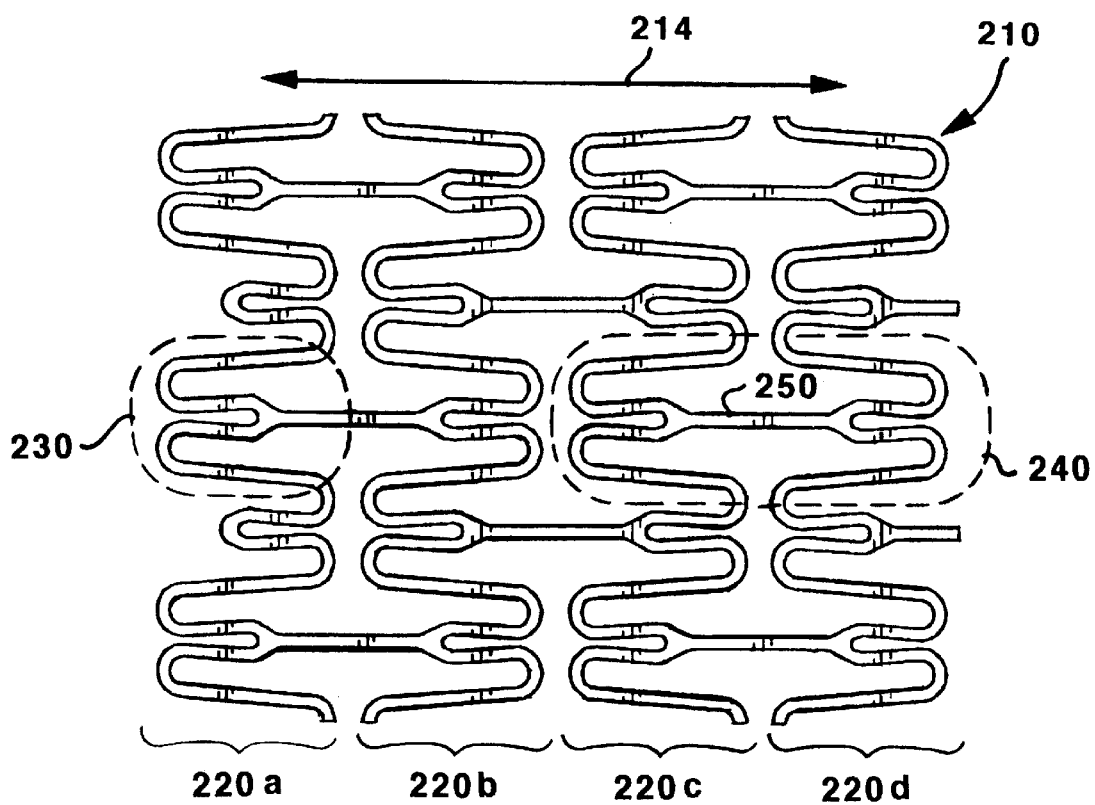
FIG. 6 is a view of a portion of another alternative stent according to the present invention.

FIG. 6 depicts another embodiment of a stent 210 according to the present invention in a plan view of a portion of the body of the stent 210 in which the body has been unrolled from the tubular shape. The stent 210 also includes cylindrical sections 220a, 220b, 220c, and 220d (collectively referred to as cylindrical sections 220) located successively along a longitudinal axis 214. Each of the cylindrical sections 220 has a length along the longitudinal axis 214 and includes a plurality of W-shaped elements 230 (only one of which is denoted by a reference number). The W-shaped elements 230 open in alternating directions along the longitudinal axis 214 of the stent 210 about the perimeter or circumference of the cylindrical sections 220 (i.e., in the hoop direction).

The cylindrical sections 220 are preferably arranged such that the W-shaped elements 230 in adjacent cylindrical sections 220 alternate between pairs of W-shaped elements 230 that open towards each other and pairs of W-shaped elements 230 that open away from each other when moving around the perimeter or circumference of the stent 210 (i.e., transverse to the axis 214 or in the hoop direction). The pairs of W-shaped elements 230 that open towards each other from adjacent cylindrical sections 220 are connected by tie members 250 to form cells 240 in a manner similar to that described above with respect to stents 10 and 110.

Figure 7:
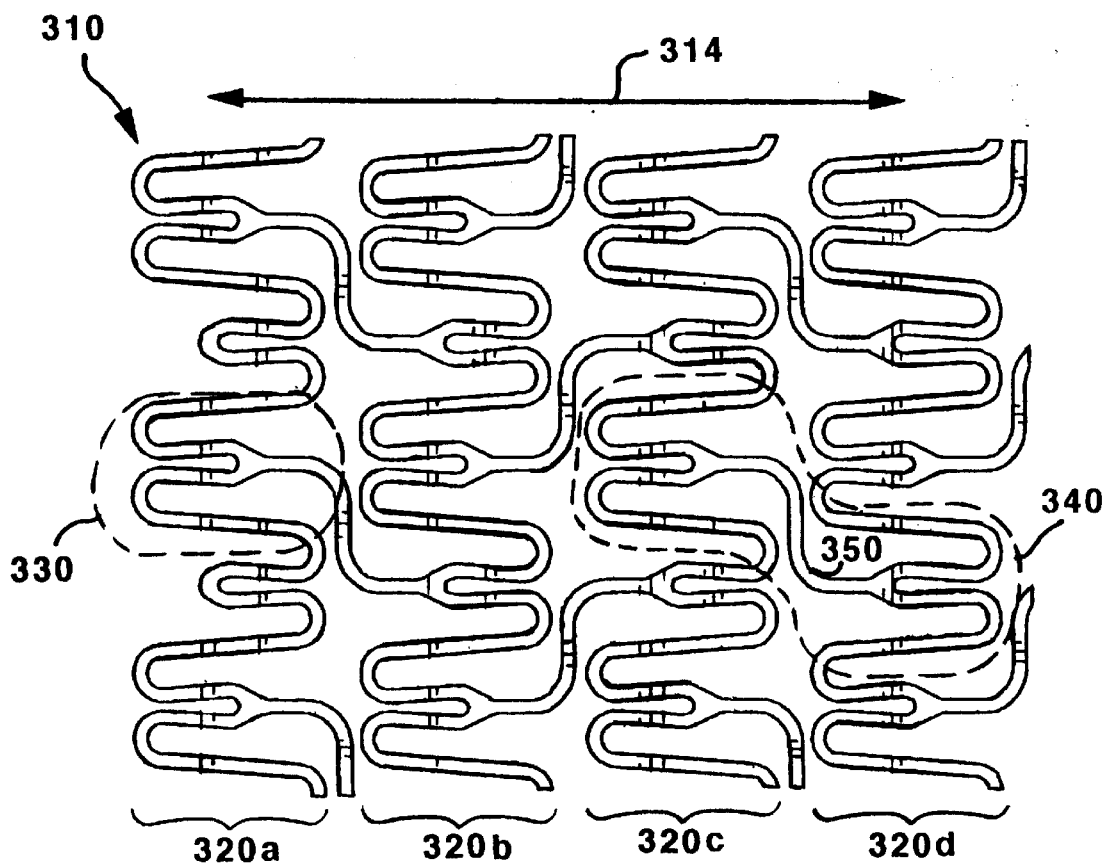
FIG. 7 is a view of a portion of another alternative stent according to the present invention.

FIG. 7 depicts another embodiment of a stent 310 according to the present invention in a plan view of a portion of the body of the stent 310 in which the body has been unrolled from the tubular shape. The stent 310 also includes cylindrical sections 320a, 320b, 320c, and 320d (collectively referred to as cylindrical sections 320) located successively along a longitudinal axis 314. Each of the cylindrical sections 320 has a length along the longitudinal axis 314 and includes a plurality of W-shaped elements 330 (only one of which is denoted by a reference number). The W-shaped elements 330 open in alternating directions along the longitudinal axis 314 of the stent 310 about the perimeter or circumference of the cylindrical sections 320 (i.e., in the hoop direction).

One difference between the design of the stent 310 and the stents described above is that the cylindrical sections have been rotated about the longitudinal axis 314 such that the W-shaped elements 330 in adjacent cylindrical sections 320 that are aligned along the longitudinal axis 314 open in the same direction. As a result, the tie members 350 are curved to attach the W-shaped elements 330 in the adjacent cylindrical sections 320 that open toward each other to form cells 340. In other words, the adjacent cylindrical sections 320 are out-of-phase with each other. In the depicted embodiment, the adjacent cylindrical sections are out-of-phase by one of the W-shaped elements 330, although it will be understood that the W-shaped elements may be out-of phase by different amounts. In contrast, the cylindrical sections of the stents 10, 110 and 210 can be described as being in-phase with the tie members 50, 150, 250 connecting W-shaped elements 30, 130, 230 to form cells 40, 140, 240 being generally aligned with the longitudinal axes of the stents 10, 110 and 210.

It will be understood that stents such as the illustrative embodiments described above may be provided as self-expanding stents or as stents that are not self-expanding, i.e., stents that must be expanded by a balloon or some other method.

The radially expandable stents depicted and described above with respect to FIGS. 1–7 can be formed as a one-piece, completely integral units from a thin-walled tube of suitable material. If so formed, the stents will be cut or machined from a tube using, e.g., laser, water jet, EDM (electrical discharge machining), chemical etching, stamping, or high velocity forming techniques. As a result, the stents can be formed without welds or joints. It is also envisioned, however, that stents according to the present invention could be formed from a sheet of material using, e.g., laser, water jet, EDM, chemical etching, stamping, or high velocity forming techniques. If the stent was formed from a sheet of material, the bodies 10/110 as seen in FIGS. 2 and 4 would be formed into a tube and welded or otherwise joined along the length of the stents. Those skilled in the art will recognize other attachment techniques including, but not limited to twisting, biocompatible adhesives, brazing, crimping, stamping, etc.

Alternatively, the stents could be manufactured from wire formed on a mandrel or through the intermeshing of gears as is known in the art. In those methods of manufacturing, the W-shaped elements of the cylindrical sections would be formed followed by welding of the successive cylindrical sections together using the tie members. Those skilled in the art will recognize other attachment techniques including, but not limited to twisting, biocompatible adhesives, brazing, crimping, stamping, etc.

Preferred materials for stents according to the present invention include those materials that can provide the desired functional characteristics with respect to biological compatibility, modulus of elasticity, radio-opacity, etc. For example, it is preferred that self-expanding stents be capable of significant recoverable strain to assume a low profile for delivery to a desired location within a body lumen. After release of the compressed self-expanding stent, it is preferred that the stent be capable of radially expanding back to its original diameter or close to its original diameter.

Particularly preferred materials for self-expanding stents according to the present invention are nickel titanium alloys and other alloys that exhibit superelastic behavior, i.e., are capable of significant distortion without plastic deformation. Stents manufactured of such materials may be significantly compressed without permanent plastic deformation, i.e., they are compressed such that the maximum strain level in the stent is below the recoverable strain limit of the material. Discussions relating to nickel titanium alloys and other alloys that exhibit behaviors suitable for stents according to the present invention can be found in, e.g., U.S. Pat. No. 5,597,378 (Jervis) and WO 95/31945 (Burmeister et al.). Nickel titanium alloys suitable for use in manufacturing stents according to the present invention can be obtained from, e.g., Memry Corp., Brookfield, Conn.

If the stents are designed to be expanded by a balloon or some other device (i.e., the stents are not self-expanding), they may be manufactured from an inert, biocompatible material with high corrosion resistance that can be plastically deformed at low-moderate stress levels, such as tantalum. Other acceptable materials include stainless steel, titanium ASTM F63-83 Grade 1, niobium or high carat gold K 19–22.

The radially outward directed force developed by the stents according to the present invention, whether self-expanding or radially-expandable, serves two functions. One function is to hold the body lumen open against a force directed radially inward, e.g., a spasm, as well as preventing restriction of the passageway through the lumen by intimal flaps or dissections generated by, e.g., prior balloon angioplasty. Another function is to fix the position of the stent within the body lumen by intimate contact between the stent and the walls of the lumen. The outwardly directed forces must not be excessive, however, to avoid traumatization of the lumen walls by the stent.

The diameters of some preferred stents when in the compressed state for delivery to a desired location within a body lumen is typically reduced from about two to about six times the diameter of the stents when in their expanded state before compression. For example, typical stents may have a compressed external diameter of about 1 millimeter to about 3 millimeters for delivery and an expanded external diameter in a body lumen of about 3 millimeters to about 15 millimeters when released from compression in a large arterial vessel. Some preferred stents used in coronary arteries may have a compressed external diameter of about 1 millimeter and an expanded external diameter in a body lumen of up to about 5 millimeters.

Figures 8, 9:
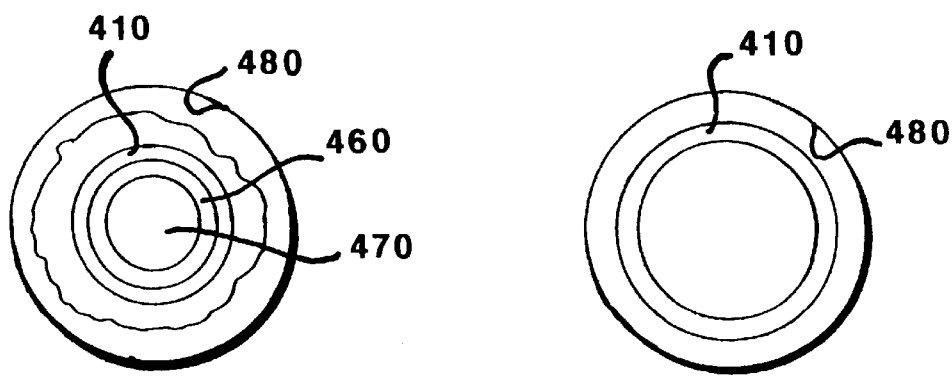
FIG. 8 is an end view of a stent located on a balloon catheter in a body lumen before deployment of the stent.
FIG. 9 is an end view of the stent of FIG. 8 after deployment and removal of the balloon catheter.

One stent 410 according to the present invention is depicted in FIG. 8 as located on a balloon 460 that is, in turn, located on a delivery catheter 470 according to methods known to those skilled in the art. For expandable stents, the stent 410 can be crimped by hand or with a suitable crimping tool (not shown) onto the balloon 460. Manually squeezing the stent 410 over the balloon 460 is also acceptable. If the stent 410 is self-expanding, the delivery system will typically include some method of containing the stent 410 in the compressed state depicted in FIG. 8 such as an outer sleeve, etc. Furthermore, if the stent 410 is self-expanding, it may be supplied without the balloon 460 located within the stent 410.

The stent 410 and balloon 470 can be transported to a desired location within the body lumen 480 via a standard guiding catheter (not shown) using known methods and procedures. Once in location, the stent 410 can be expanded radially by inflating the balloon 460 to force the stent 410 against the inner surface of the lumen 480 using standard angioplasty procedures and techniques. It is preferred that the expanding balloon 460 together with the stent 410 compresses the plaque in the stenosis located in the lumen 480 to reduce the chance of reocclusion of the lumen 480.

FIG. 9 depicts the stent 410 in its expanded state in contact with the lumen 480 after the balloon 460 and its associated catheter 470 have been removed. When the angioplasty procedure is completed, balloon 460 is deflated and withdrawn along with its catheter 470, leaving stent 410 firmly implanted within lumen 480. Previously occluded lumen 480 is recannalized and patency is restored. It is preferred that the stent 410 be firmly implanted and imbedded in compressed plaque in the lumen 480, providing adequate support to the lumen 480.

The preceding specific embodiments are illustrative of the practice of the invention. It is to be understood, however, that other expedients known to those skilled in the art or disclosed herein, may be employed without departing from the scope of the appended claims.

| No. | Component |
| --- | --- |
| 10 | Stent |
| 12 | Passageway |
| 14 | Longitudinal Axis |
| 20a–20e | Cylindrical Sections |
| 30a/30b | W-shaped Elements |
| 32a/32b | Outside Legs |
| 34a/34b | Outside Legs |
| 36a/36b | Center Sections |
| 37/37a/37b | Apexes of Center Sections |
| 40a–40c | Cells formed by W-shaped Elements |
| 50 | Tie Members |
| 110 | Stent |
| 112 | Passageway |
| 114 | Longitudinal Axis |
| 120a–120e | Cylindrical Sections |
| 130a/130b | W-shaped Elements |
| 132a/132b | Outside Legs |
| 134a/134b | Outside Legs |
| 136a/136b | Center Sections |
| 137a/137b | Apex of Center Sections |
| 140a–140c | Cells formed by W-shaped Elements |
| 150 | Tie Members |
| 210 | Stent |
| 214 | Longitudinal Axis |
| 220a–220d | Cylindrical Sections |
| 230 | W-shaped Elements |
| 240 | Cell formed by W-shaped Elements |
| 250 | Tie Members |
| 310 | Stent |
| 314 | Longitudinal Axis |
| 320a–320d | Cylindrical Sections |
| 330 | W-shaped Elements |
| 340 | Cell formed by W-shaped Elements |
| 350 | Tie Members |
| 410 | Stent |
| 460 | Balloon |
| 470 | Delivery Catheter |
| 480 | Lumen |

What is claimed is:

1. A radially expandable stent for implantation within a body vessel, comprising:

a plurality of cylindrical sections successively arranged along a longitudinal axis of the stent;

a plurality of W-shaped elements in each of the cylindrical sections, each of the W-shaped elements comprising a center section and two outside legs, the plurality of W-shaped elements in each of the cylindrical sections opening in alternating directions along the longitudinal axis of the stent, wherein the W-shaped elements in adjacent cylindrical sections alternate between pairs of W-shaped elements that open towards each other along the longitudinal axis and pairs of W-shaped elements that open away from each other along the longitudinal axis when moving about the circumference of the adjacent cylindrical sections; and a plurality of tie members connecting adjacent cylindrical sections along the longitudinal axis of the stent, the tie members connecting center sections of the pairs of W-shaped elements that open towards each other along the longitudinal axis in each pair of adjacent cylindrical sections.

2. A stent according to claim 1, wherein the center section of each of the W-shaped elements is shorter in the longitudinal direction than the outside legs of the W-shaped element.

3. A stent according to claim 1, wherein the center section of each of the W-shaped elements have a longitudinal length that is about half of the longitudinal length of the outside legs of the W-shaped element.

4. A stent according to claim 1, wherein the stent comprises first, second, and third cylindrical sections arranged along the longitudinal axis in that order, and further wherein the tie members connecting the center sections of the pairs of W-shaped elements that open towards each other in the first and second cylindrical sections are offset about the circumference of the stent from the tie members connecting the centers of the pairs of W-shaped elements that open towards each other in the second and third cylindrical sections.

5. A stent according to claim 1, wherein the center section of each of the W-shaped elements is connected to the outside legs of the W-shaped element with rounded bends.

6. A stent according to claim 1, wherein the cylindrical sections are in-phase with each other.

7. A stent according to claim 1, wherein the cylindrical sections are out-of-phase with each other.

8. A radially expandable stent for implantation within a body vessel, comprising:

a plurality of cylindrical sections successively arranged along a longitudinal axis of the stent;

a plurality of W-shaped elements in each of the cylindrical sections, each of the W-shaped elements comprising a center section and two outside legs, wherein the center section of each of the W-shaped elements is shorter in the longitudinal direction than the outside legs of the W-shaped element, the plurality of W-shaped elements in each of the cylindrical sections opening in alternating directions along the longitudinal axis of the stent, wherein the W-shaped elements in adjacent cylindrical sections alternate between pairs of W-shaped elements that open towards each other along the longitudinal axis and pairs of W-shaped elements that open away from each other along the longitudinal axis when moving about the circumference of the adjacent cylindrical sections; and a plurality of tie members connecting adjacent cylindrical sections along the longitudinal axis of the stent, the tie members connecting center sections of the pairs of W-shaped elements that open towards each other along the longitudinal axis in each pair of adjacent cylindrical sections;

wherein the stent comprises first, second, and third cylindrical sections arranged along the longitudinal axis in that order, and further wherein the tie members connecting the center sections of the pairs of W-shaped elements that open towards each other in the first and second cylindrical sections are offset about the circumference of the stent from the tie members connecting the centers of the pairs of W-shaped elements that open towards each other in the second and third cylindrical sections.

9. A stent according to claim 8, wherein the center section of each of the W-shaped elements is connected to the outside legs of the W-shaped element with rounded bends.

10. A stent according to claim 8, wherein the cylindrical sections are in-phase with each other.

11. A stent according to claim 8, wherein the cylindrical sections are out-of-phase with each other.

12. A method of implanting a radially expandable stent within a body lumen comprising the steps of:

a) providing the radially expandable stent in a compressed state comprising:

a plurality of cylindrical sections successively arranged along a longitudinal axis of the stent, a plurality of W-shaped elements in each of the cylindrical sections, each of the W-shaped elements comprising a center section and two outside legs, the plurality of W-shaped elements in each of the cylindrical sections opening in alternating directions along the longitudinal axis of the stent, wherein the W-shaped elements in adjacent cylindrical sections alternate between pairs of W-shaped elements that open towards each other along the longitudinal axis and pairs of W-shaped elements that open away from each other along the longitudinal axis when moving about the circumference of the adjacent cylindrical sections; and a plurality of tie members connecting adjacent cylindrical sections along the longitudinal axis of the stent, the tie members connecting center sections of the pairs of W-shaped elements that open towards each other along the longitudinal axis in each pair of adjacent cylindrical sections;

b) advancing the stent to a desired location within a body lumen; and c) radially expanding the stent within the body lumen.

13. A method according to claim 12, wherein the center section of each of the W-shaped elements is shorter in the longitudinal direction than the outside legs of the W-shaped element.

14. A method according to claim 12, wherein the center section of each of the W-shaped elements have a longitudinal length that is about half of the longitudinal length of the outside legs of the W-shaped element.

15. A method according to claim 12, wherein the stent comprises first, second, and third cylindrical sections arranged along the longitudinal axis in that order, and further wherein the tie members connecting the center sections of the pairs of W-shaped elements that open towards each other in the first and second cylindrical sections are offset about the circumference of the stent from the tie members connecting the centers of the pairs of W-shaped elements that open towards each other in the second and third cylindrical sections.

16. A method according to claim 12, wherein the center section of each of the W-shaped elements is connected to the outside legs of the W-shaped element with rounded bends.

17. A method according to claim 12, wherein the cylindrical sections are in-phase with each other.

18. A method according to claim 12, wherein the cylindrical sections are out-of-phase with each other.

* * * * *